(12) United States Patent
Bevirt et al.

(10) Patent No.: US 6,193,102 B1
(45) Date of Patent: Feb. 27, 2001

(54) PLATE STACKER APPARATUS

(75) Inventors: JoeBen Bevirt, Emerald Hills; Gabriel Noah Brinton, Palo Alto, both of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/303,381

(22) Filed: Apr. 30, 1999

(51) Int. Cl.⁷ .............................. G07F 11/00; B65H 1/00
(52) U.S. Cl. ................... 221/2; 221/197; 221/287
(58) Field of Search ................ 221/2, 123, 197, 221/210, 220, 236, 238, 287, 289, 298, 311, 93

(56) References Cited

U.S. PATENT DOCUMENTS

| | | | |
|---|---|---|---|
| 3,300,090 | * 1/1967 | Carden | 221/298 X |
| 3,443,706 | * 5/1969 | Puhm | 221/298 X |
| 3,752,361 | * 8/1973 | VanLiner et al. | 221/298 X |
| 4,747,390 | * 5/1988 | Storm | 221/298 X |
| 5,105,980 | * 4/1992 | Hofmann | 221/236 X |
| 5,328,258 | * 7/1994 | Scalise | 221/298 X |
| 5,335,810 | * 8/1994 | Holloway | 221/289 X |
| 5,788,114 | * 8/1998 | Perego | 221/281 X |
| 6,004,020 | * 12/1999 | Bartur | 221/123 X |

OTHER PUBLICATIONS

SD5000 Cartesian Technologies Stacker & Destacker System Internet Page.
PegaSys™ 320 Cartesian Technologies Dual Conveyor Liquid Transfer System Internet Page.
PlateStak™ Carl Creative Systems, Inc. Internet Page.
PlateTrak™ Carl Creative Systems, Inc. Internet Page.
"About CCS" Carl Creative Systems, Inc. Internet Page.

* cited by examiner

Primary Examiner—Christopher P. Ellis
Assistant Examiner—Gene O. Crawford
(74) Attorney, Agent, or Firm—Howrey Simon; Arnold & White, LLP

(57) ABSTRACT

A plate stacker is described for use in the field of sample analysis. The plate stacker increases the rate and ease with which sample carriers such as microwell plates may be interfaced with an automated system and includes a removable rack attached to a base to allow plates to be transported to and from an automated system. The stacker rack includes a door which allows for a compact stacker thus allowing manipulation of the microwell plates in a compact area. Generally, the plate stacker provides a means to allow a user to interface with an automated system. The rack portion of the stacker allows the user to load and unload microwell plates into the system in batches by loading or unloading multiple individual plates into or out of the rack. The base portion allows the automated system to load and unload individual microwell plates from the stacker.

36 Claims, 8 Drawing Sheets

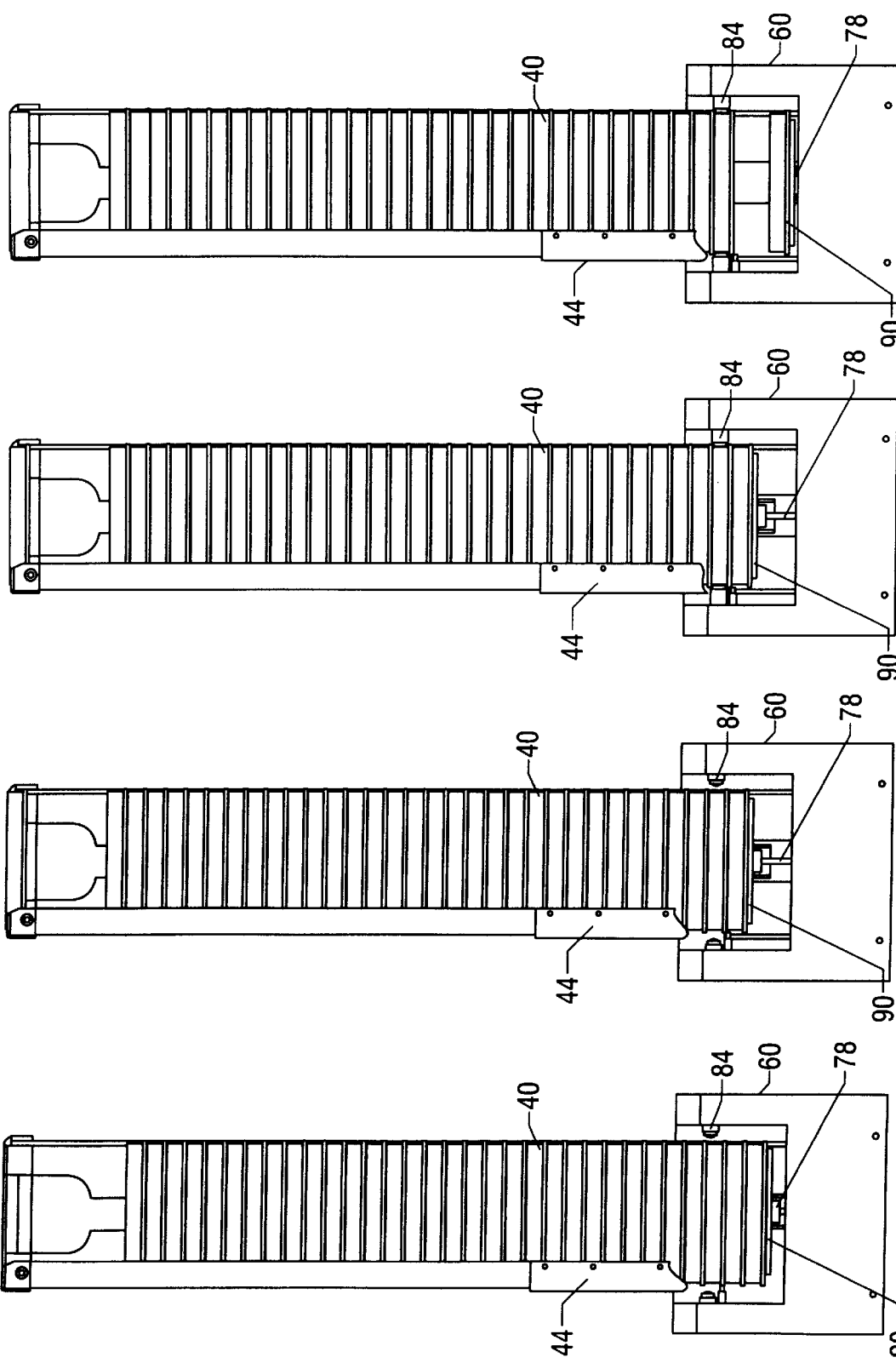

PLATE STACKER APPARATUS

BACKGROUND OF THE INVENTION

1. Field of the Invention

The invention relates to the field of sample analysis. More particularly, this invention relates to an apparatus and method for increasing the rate at which microwell plates can be manipulated in performing various experiments.

2. Description of the Related Art

In the field of molecular biology, the process of sequencing nucleic acids has become significant as more and more diseases are linked to genetic abnormalities. The process of identifying genes and their corresponding proteins for potential therapeutic applications is well known.

Other types of molecular biology procedures are also important for therapeutic and research purposes including DNA restriction mapping, DNA probe generation, replication, DNA sample processing, and cycle sequencing. Generally, these procedures involve a substantial number of steps including, without limitation, automated liquid handling, robotic movement of the samples, pipetting of small amounts of many different reagents into a sample, and heating the samples within a given temperature range. These protocols includes a lengthy series of steps which must be performed in the correct order with absolute precision. Further, such assays are often done on multiple samples that require the manipulation of samples in sample carriers in a uniform fashion.

For instance, during clinical analysis of blood chemistry, various reagents and catalysts are mixed with blood samples in given amounts and in particular sequences. This analysis can yield the level of HDL cholesterol, LDL cholesterol, lipids, etc. present in the blood. By having multiple samples in a sample carrier, several samples may be analyzed at any give time. Similarly, in the area of new drug discovery, it is desirable to investigate numerous candidates for therapeutic agents. Given the great number of potential candidates, automated testing is desirable.

Because of the expense of the equipment required to perform these protocols accurately, increasing the throughput of the equipment performing these protocols becomes important for laboratories such as microbiology laboratories. It is desirable to increase the rate at which these protocols are performed while retaining, or even increasing, the quality of performance of the protocols. Automation is one method by which the rate of performing the protocols may be increased. By increasing the rate at which these protocols are performed, the protocols may be performed at a reduced price.

Regardless of the type of experiment to be performed, sample carriers are generally employed so that more than one sample may be processed at any given time. For example, microwell plates are generally utilized in these sample analysis protocols. Microwell plates are plastic plates containing uniformly-spaced cavities for holding various liquids. Generally, these commercially available microwell plates contain eight rows of twelve microwells for an industry-standard ninety-six microwell plate, or sixteen rows of twenty-four microwells for an industry-standard three hundred eighty-four microwell plate. Other sizes are also commercially available.

It is generally known to perform a protocol with automation as follows. Multiple microwell plates are stacked in one location. A transfer mechanism transfers one the of the microwell plates onto a conveyor. The conveyor transports the microwell plate to the desired station, e.g. a pipetting station. The conveyor then takes the microwell plate to the next station, and so on until the desired protocol has been performed on that microwell plate. Upon completion, that microwell plate is transferred by another transfer mechanism to a completion area for further processing.

To transport and store multiple microwell plates, it is known to stack these microwell plates on top of one another. In fact, most microwell plates are designed for stacking.

In many experiments, it is important to maintain a constant, or even a germ-free, environment. Thus, it is often desired to enclose the samples and the automation equipment. Therefore, it is often desired to minimize the size of equipment, thus minimizing the size of the area that needs to be enclosed.

Current microwell stackers, such as the Cartesian Technologies Stacker and Destacker System SD5000, secure a stack of microwell plates on all four corners. This is a disadvantage. Sometimes it is necessary to remove a plate from the middle of a stack of plates. For example, if it is discovered that the plates have been stacked in an incorrect order, a microwell plate located in the middle of the stack may need to be removed. However, because the plates are secured on all four sides, the only way to remove the plate in the middle of the stack is to remove all of the microwell plates above that plate as well. Once the incorrectly loaded plate is removed, the remaining plates must then be reloaded into the stack. This process is inefficient and time-consuming.

Another problem with current stackers is that current stackers are generally fixedly mounted on top of a transfer mechanism. Thus, it is not possible to load the stack of microwell plates in one area, and then locate that stack onto the transfer mechanism: both the stacker and the transfer mechanism must be manipulated together.

Another problem with the current stackers is their inability to determine the orientation of each microwell plate. It is generally known that each microwell plate is typically manufactured such that one of its four corners is chamfered. Yet current stackers are not capable of recognizing the plate orientation. This increases the likelihood that an operation may be performed on the wrong cavity in a plate.

Thus, despite years of effort, the method of manipulating sample carriers such as microwell plates to perform various protocols continues to be slower and more expensive than would be desired.

The present invention is directed to overcoming, or at least reducing the effects of, one or more of the problems set forth above.

SUMMARY OF THE INVENTION

In accordance with an aspect of the present invention, there is provided a rack for storing, transporting, dispensing, and/or restacking sample carriers, comprising three vertical corner sections each having a top end and a bottom end and a door functionally associated with said bottom end of one of said corner sections to allow access to said microwell plate. In some aspects, the rack further comprises two rack support brackets, each rack support bracket attached to the bottom end of a vertical corner sections. In other aspects, each rack support brackets is further provided with a cylindrical opening.

In some embodiments, the rack has only three sides. This is advantageous since it allows for the removal of a microwell plate in the middle of the stack.

In some embodiments, the rack also has a door. This is advantageous for at least two reasons. First, this door generally remains closed, allowing for the rack to be carried without releasing any microwell plates. Secondly, this door can be opened to dispense the microwell plates. Thus, plates may be manipulated while remaining in the rack. This allows for a more compact design than prior art stackers.

In accordance with another aspect of the present invention, a stacker apparatus is provided for storing, transporting, reloading, and dispensing microwell plates, comprising a rack having three vertical corner sections, each vertical corner section having a top end and a bottom end; a door functionally associated with said bottom end of one of said corner sections to allow access to said microwell plate; a base adapted to receive said rack, said base further comprising a stacker table functionally associated with said base; a door opening element attached to said base, said element being positioned to contact said door on said rack; a plate gripper movably attached to said base; said rack detachably mounted to said base; each of said bottom ends of said corner sections of said rack being closer to said base than the top end of each of the corner sections; and a control functionally associated with said base.

In some aspects, a plate orientation sensor is attached to the base. Thus, in some embodiments, accuracy of processing of samples is increased because the orientation of each plate may be checked prior to processing the samples.

With prior art stackers, if the bottom plate were removed from its position in the rack, the gravity would force the remaining plates (loaded above the removed plate) to freely fall possibly spilling portions of the sample in each cavity. In some embodiments of this invention, grippers prevent this jolting of plates remaining in the stacker. Thus, the liquid samples in the plates in the stacker are less likely to be spilled.

In some embodiments, the rack is removable. This allows the rack to be loaded in one location and then transported to the work area where the protocols are to be performed. Once performed, the samples may be returned to the rack and the rack removed to another area for further processing.

This is advantageous for another reason: by having the rack removable, it is possible to properly sterilize the rack (via heat or chemical treatment) away from the experimental area. Such sterilization is important, for example, when handling biological samples.

Further, because in some embodiments the invention is more compact than current systems, the overall size of the equipment required to perform various protocols is reduced. This is advantageous since many protocols must often be performed in a germ-free environment. Thus, it is often necessary to enclose the area in which these protocols are performed. For this reason, it is desirable to have the associated work area, including the stackers, as small as possible. With prior art stackers, because the four corners of the stackers are rigid, the transfer mechanism must be located outside of the stacker rack area. However, an advantage of these embodiments is that the transfer mechanism can be located inside the stacker rack area for a more compact design In some aspects, a stacker is provided for storing, transporting, restacking, and dispensing microwell plates, comprising means for storing microwell plates, said means having three vertical corner sections; means for supporting said means for storing microwell plates further comprising a stacker table functionally associated with said means for supporting; means to grip microwell plates; means for removably attaching said means storing microwell plates to said means for supporting; means for controlling the means for storing and means for supporting to load, unload, and store the microwell plates.

In another aspect, a method is provided for storing, dispensing, and transporting microwell plates, comprising providing a rack having three vertical corner sections; providing a base adapted to receive the rack; and controlling said rack and said base to manipulate said microwell plates. In others aspects, the invention relates to a method of storing, dispensing, and transporting microwell plates, comprising providing a stacker comprising a rack having three vertical corner sections, each vertical corner section having a top end and a bottom end; a door functionally associated with said bottom end of one of said corner sections to allow access to said microwell plate; a base adapted to receive said rack, said base further comprising; a stacker table functionally associated with said base; a door opening element attached to said base positioned to contact said door on said rack; a plate gripper movably attached to said base; said rack detachably mounted to said base; each of said bottom ends of said corner sections of said rack being closer to said base than the top end of each of the corner sections; and a control functionally associated with said base; and operating the control to manipulate the microwell plates.

BRIEF DESCRIPTION OF THE DRAWINGS

FIGS. 3A–3D illustrates how one embodiment of the invention operates:

FIG. 3A shows an embodiment with a stacker table in its lowest position.

FIG. 3B shows the embodiment of FIG. 3A with a stacker table in its upper most position.

FIG. 3C shows the embodiment of FIG. 3A with a stacker table in its upper most position and grippers extended to touch a microwell plate.

FIG. 3D shows the embodiment of FIG. 3A in which grippers are extended and support microwell plates while a stacker table is in its lowest position.

Figure 1A:
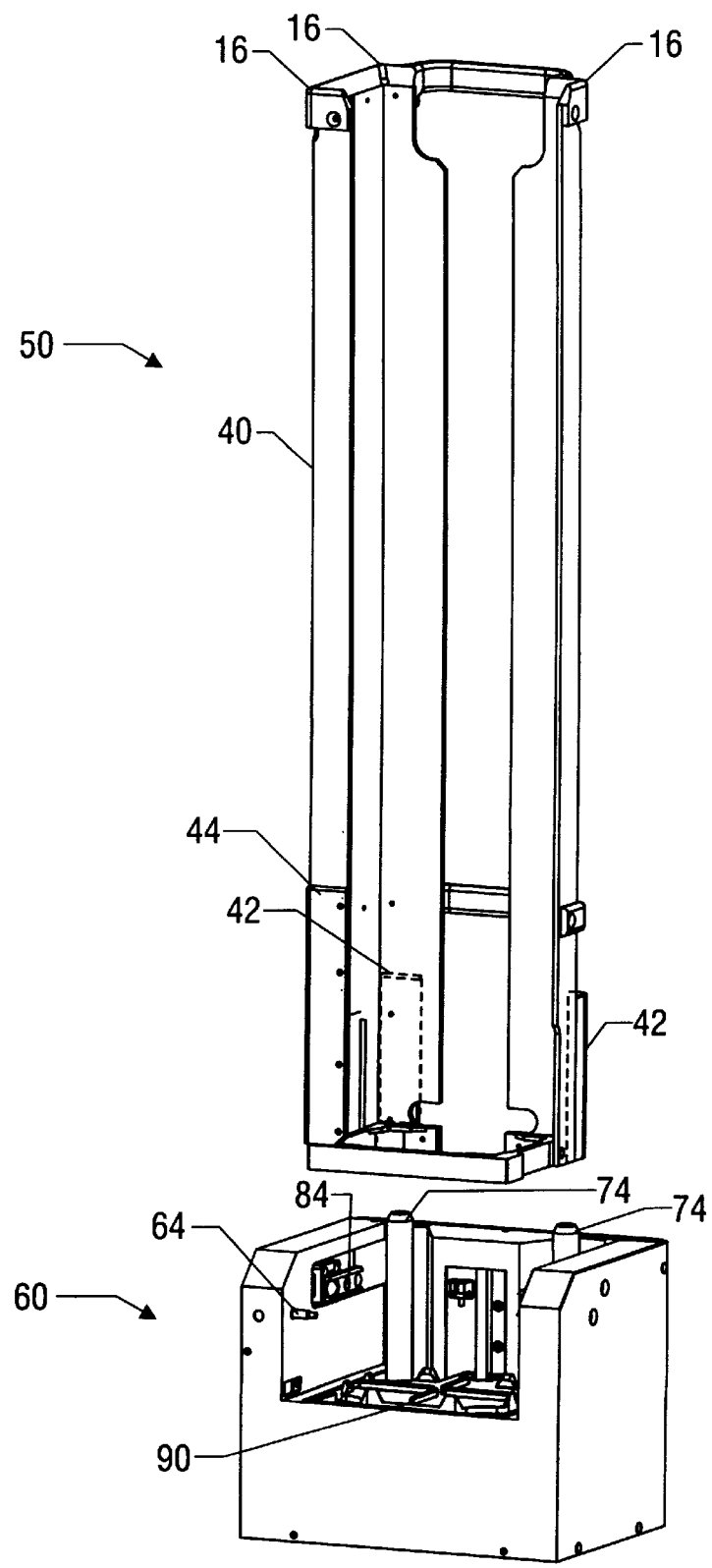
FIG. 1A illustrates two embodiment of the invention showing both a rack and a base.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Illustrative embodiments will now be described with reference to the accompanying figures.

The invention relates to an apparatus and a method to increase the throughput of manipulating microwell plates when performing various protocols. The invention increases throughput while remaining compact in size. Further aspects and advantages of the invention will become apparent from consideration of the following description and drawings.

FIG. 1A shows two embodiments of the invention: rack 40 and stacker 50. Rack 40 has three vertical corner sections 16. Door 44 is located on one end of one vertical corner section 16—the end closest to the stacker base 60. Door 44 is operably attached to corner section 16 and is capable of opening by sliding up corner section 16. In this way, when rack 40 is loaded with microwell plates, the microwell plates are may be removed when door 44 is open. When door 44 is closed, i.e. when rack 40 is removed from base 60, door 44 is closed. This prevents microwell plates from falling out of rack 40 when rack 40 is being transported.

Figure 1B:
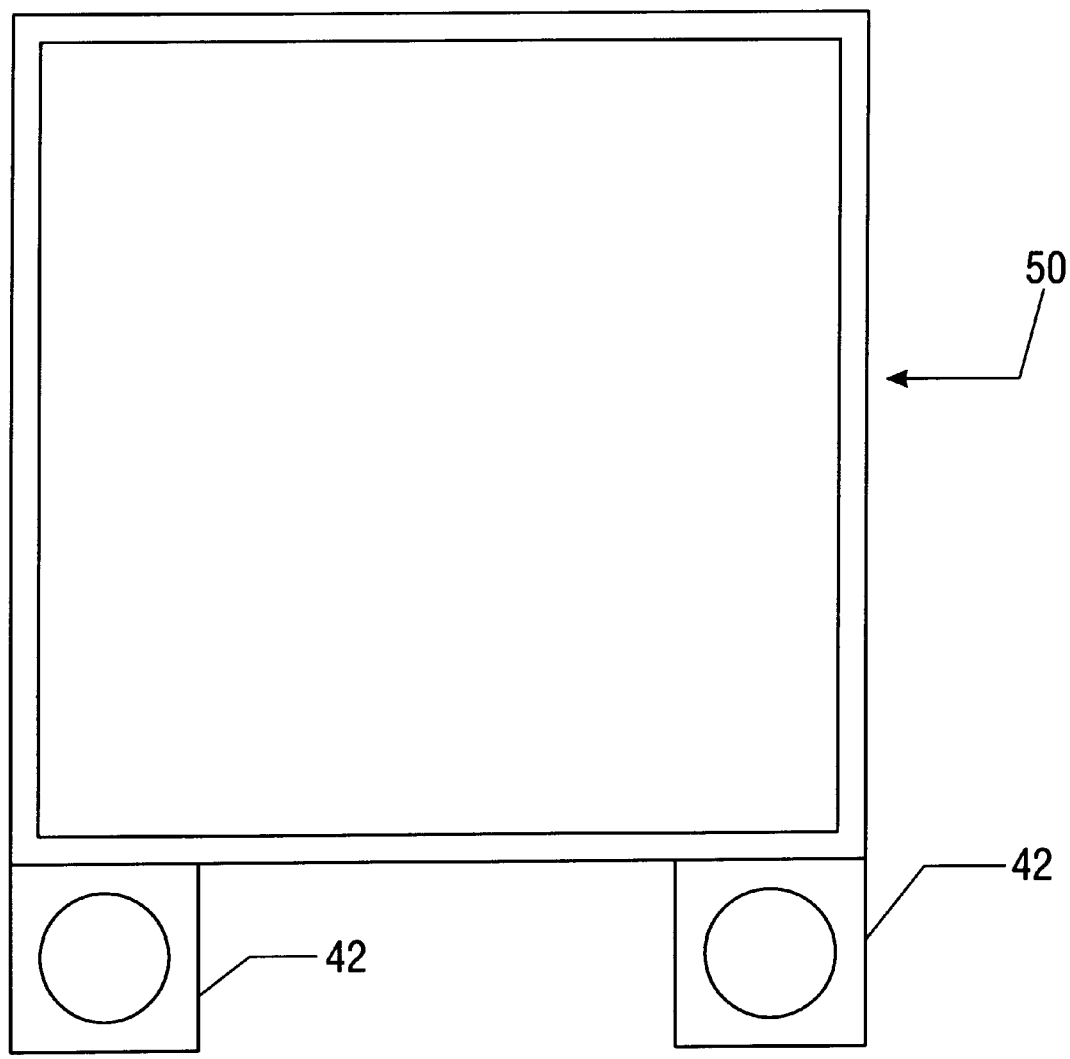
FIG. 1B illustrates a simplified bottom view of the rack of the embodiments shown in FIG. 1A.

Also mounted on rack 40 are rack support brackets 42. FIG. 1B illustrates that support brackets 42 have cylindrical holes which can be used to secure the rack 40 when used with a base. Although the female portion of the mating means is shown to be on rack 40 as support brackets 42 and the male portion of the mating means is shown to reside on base 60, any type of mating means could be used. For instance, the male portion of the mating means could be mounted on rack 40 to mate in a female arrangement on base 60. Alternatively, rack locating pins 74 are shown to reside within housing 76. However, rack locating pins 74 could be located on the outside of the housing. Further, any number of rack locating pins could be used to attach rack 40 to base 60 via an equal number of rack support brackets.

Stacker 50 is shown to be comprised of rack 40 and stacker base 60. Shown on stacker base 60 are rack locating pins 74, plate grippers 84, rack door opening element 64, and stacker table 90. In operation rack 40 is removably attached to stacker base 60 in the following manner. When loading the rack 40, as rack 40 is brought closer to stacker base 60, the rack locating pins 74 on stacker base 60 are inserted into rack support brackets 42 on rack 40. In this way, rack locating pins 44 serve to align rack 40 with stacker base 60.

When rack 40 is separated from stacker base 60, door 44 on rack 40 is in its closed position as shown in FIG. 1A. When rack 40 is inserted into stacker base 60 as described above, door 44 comes into contact with rack door opening element 64. As rack 40 is further inserted into stacker base 60, door 44 is opened. By opening this door, microwell plates are exposed at the base of rack 40. Because of this easy accessibility, the mechanisms which manipulate the microwell plates can be mounted compactly within the stacker base 60.

Figure 1C:
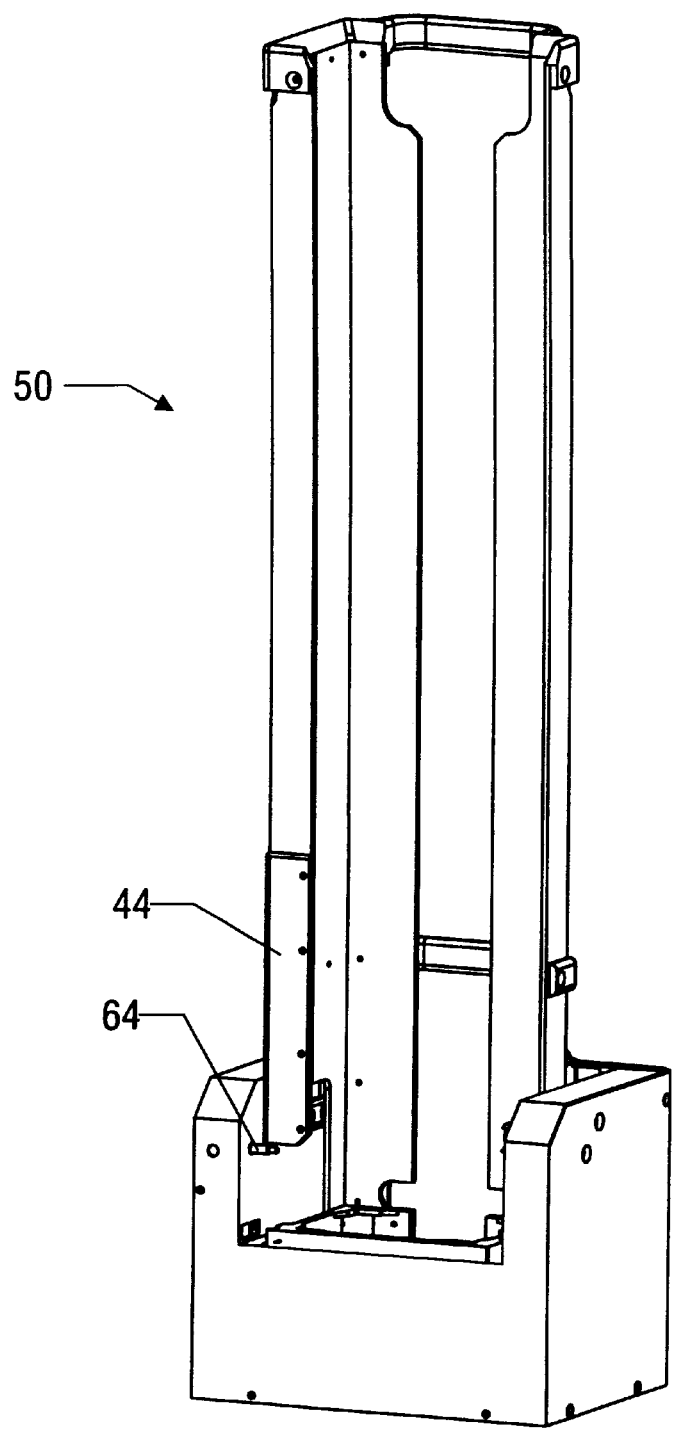
FIG. 1C illustrates an embodiment with a rack inserted into a base.

FIG. 1C shows stacker 50 when rack 40 is inserted into stacker base 60. In this position, rack door opening element 64 contacts door 44. Thus, in FIG. 1B, door 40 is in its open position.

Figure 1D:
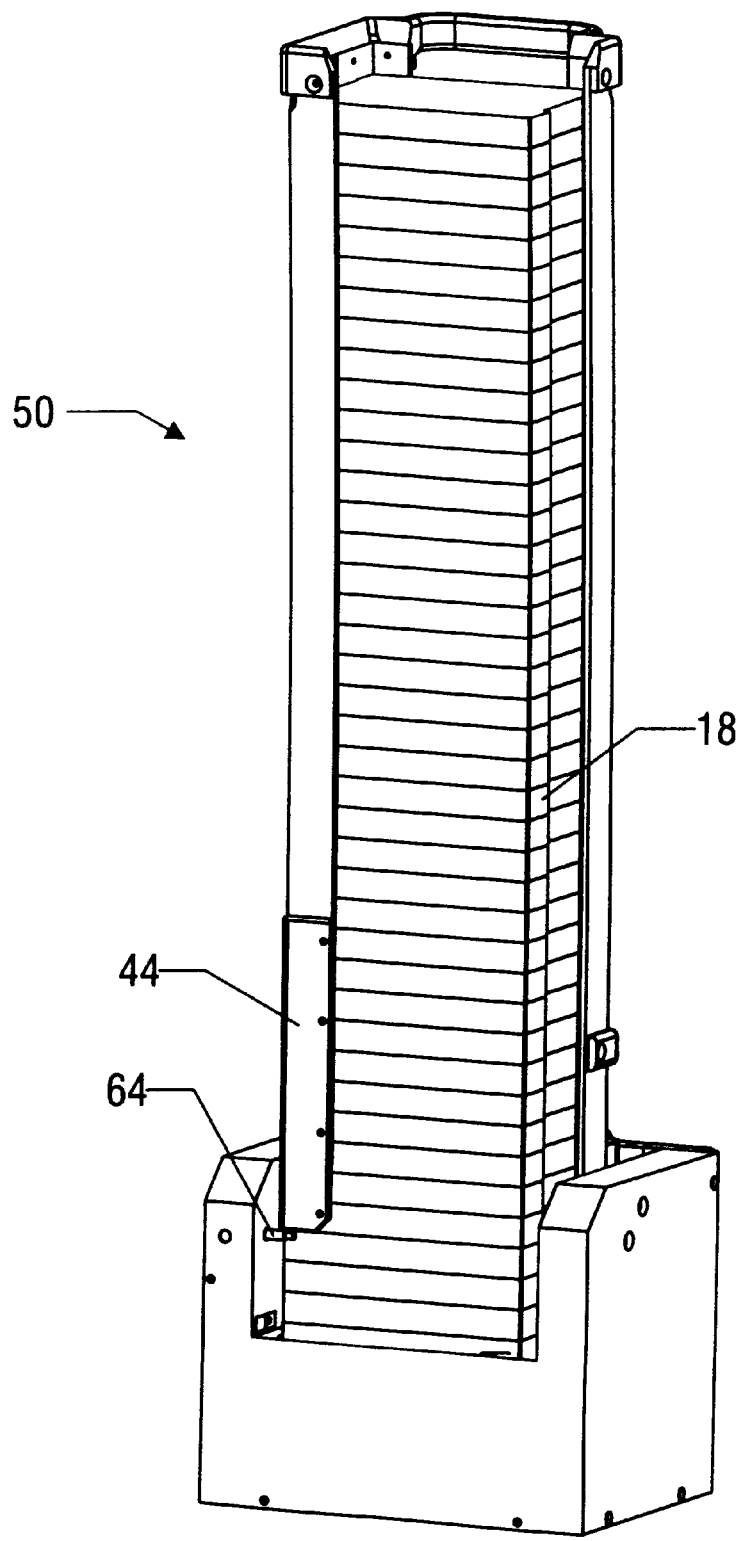
FIG. 1D illustrates the embodiment shown in FIG. 1C with microwell plates loaded into the rack.

FIG. 1D shows stacker 50 with rack 40 inserted into stacker base 60. Multiple microwell plates 18 are shown loaded into rack 40.

Previous stackers have four sides or corner sections. In these four-sided stackers, microwell plates must be inserted from the top of the stacker. Thus, if it is desired to remove the microwell plate located in the middle of a stack of a loaded prior art stacker, all of the microwell plates above the one to be removed must also be removed. This is time-consuming and inefficient. The embodiment in FIG. 1 alleviates the need to remove multiple plates. Rack 40 with only three corner sections 16, allows removal of one plate by simply rotating that to be removed, and removing it through the opening in rack 40. While the plates above the one to be removed must be raised in the stack, these plates do not have to be totally removed to remove one plate.

This would not be possible in a prior art rack in which four sides were present because the fourth side, missing from the embodiment shown, would not allow for removal of a microwell plate in this fashion.

Also, another advantage to these embodiments shown in FIG. 1 is that rack 40 is removable from stacker base 60. The removability of rack 40 from stacker base 60 permits rack 40 to be loaded and unloaded by an operator (not shown) at an entirely different location than the stacker location. This advantage allows an operation to be designed to have one central loading area and another unloading area which can be entirely different from the location of the stacker. Further, rack 40 can be removed from stacker base 60 so that rack 40 may be properly sanitized in an oven or in chemical bath. This provides desirable flexibility to the layout of the work area.

Figure 2A:
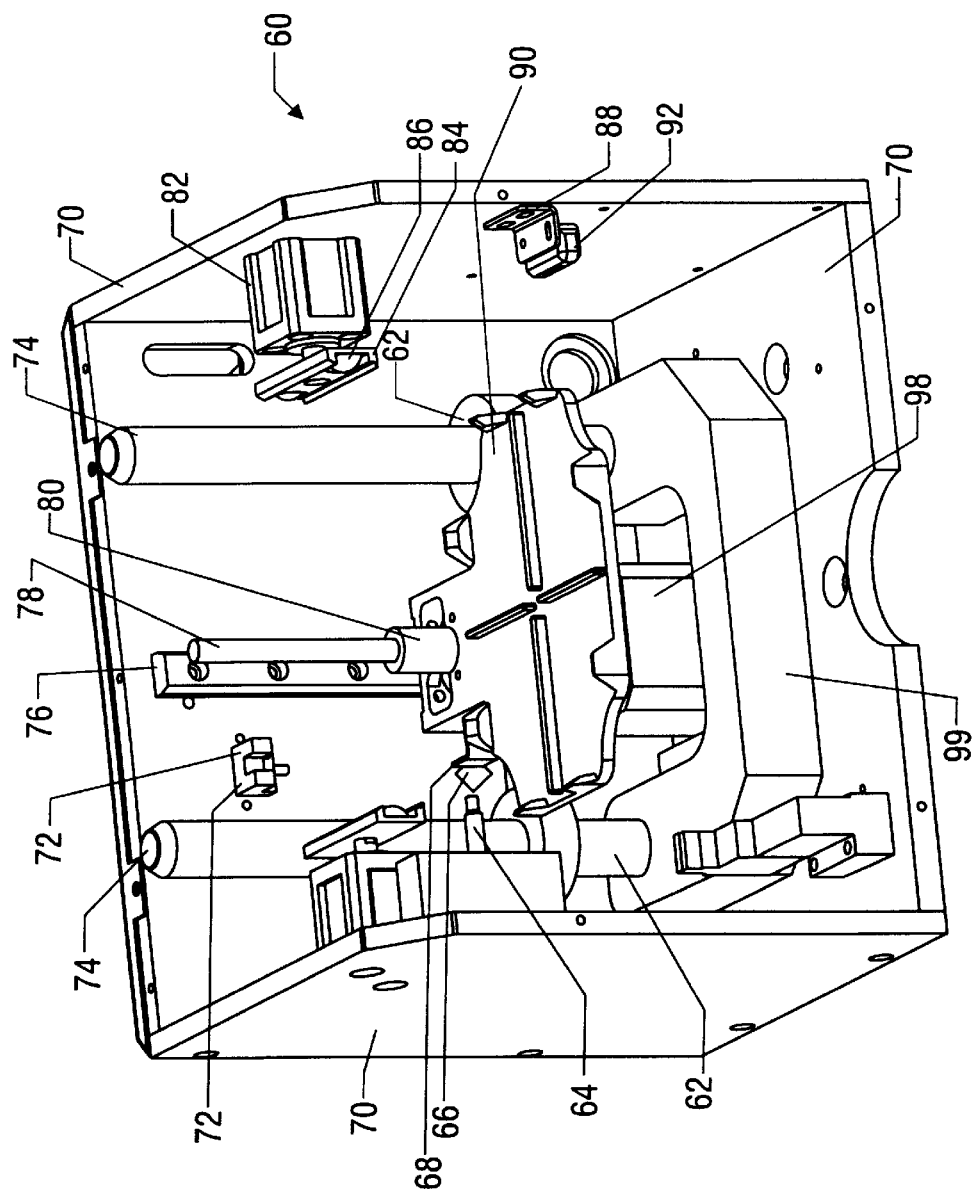
FIG. 2A details the components in a base of an embodiment of the invention.

Referring now to FIG. 2A, a detailed view of stacker base 60 is shown. Two rack locating pins 74 are shown which can be used to properly align a rack. Any type of mating means, however, could be utilized. For example, the male portion of the mating means could be mounted on rack 40 to mate in a female arrangement on base 60. Alternatively, rack locating pins 74 are shown to reside within housing 76. However, rack locating pins 74 could be located on the outside of the housing. Further, any number of rack locating pins could be used to attach rack 40 to base 60 via an equal number of rack support brackets.

As rack 40 is inserted into stacker base 60, rack support brackets 42 on rack 40 circumscribe rack locating pins 74. If a rack is lowered onto stacker base 60, the rack can come to rest on means for supporting a rack at a prescribed height. In this embodiment, shaft collar 62 support rack 40 (not shown) at a prescribed height. Shaft collar 62 circumscribe rack locating pin 74 as shown. However, any type of means for supporting a rack could be utilized such as a nut, or projections attached to the rack instead of the base.

At the bottom of stacker base 60 is stacker base floor 96. Resting on stacker housing 70 is stacker base support 99 to which shaft locating pins 74 are mounted. Although stacker base support 99 is shown in this embodiment, stacker base support 99 is not necessary for the invention to operate properly. However, stacker base support 99 can provide extra support for rack locating pins 74 and thus for rack 40. Raising means 98 is surrounded by stacker base support 99. Raising means 98 can include without limitation a readily commercially available stepper motor, although any type of elevation systems such as pneumatics, hydraulic systems, would suffice. Movably attached to the top of raising means 98 is stacker table 90. In operation, raising means 98 drives stacker table 90 up and down in the following manner: raising means 98 rotates lead screw 78. Lead screw 78 is attached to stacker table 90 by lead screw nut 80. Lead screw nut 80 is attached to stacker table 90. Thus stacker table 90 travels up and down as raising means 98 rotates lead screw 70 in a conventional lead screw arrangement. Alternatively, if another types of raising means is used, such as pneumatics, simple pistons may replace lead screw 78 to raise and lower stacker table 90.

To provide additional support for stacker table 90, stacker table 90 may be movably attached to linear bearing 76 which is attached to housing 70 as shown. Thus, linear bearing 76 can provide stability for stacker table 90 as it travels up and down.

When rack 40 (not shown) is inserted to stacker base 60, the microwell plates are supported by stacker table 90. As stacker table 90 travels up and down, so do the microwell plates.

Base 60 may also provide means for limiting the travel of stacker table 90. For instance in FIG. 2A travel limit sensor 22, home sensor 66, and sensor tab 68 can send signals to a controller which in turn controls to power to raising means 98. Sensor tab 68 may be attached to stacker table 90. Thus, as stacker table 90 travels up and down, so does sensor tab 68. The position of the stacker table 90 is controlled by stacker control. The travel limit sensor and the home sensor allow the controller to detect the location of stacker table 90.

When stacker table 90 is in its lowest position, i.e., nearest to stacker base floor 96, sensor tab 68 comes near enough to home sensor 66 such that home sensor 66 detects sensor tab 68. Home sensor 66 then sends a signal to stacker control that stacker table 90 has reached its home position. Stacker control therefore will turn off raising means 98 so that stacker table will remain in its home position. When it is desired for the stacker table to raise both itself and the microwell plates it is supporting to their higher position, i.e., the position farthest away from stacker base floor 96, stacker control will turn on raising means 98 which drives stacker table upward. Raising means 98 continues to turn lead screw 78 until sensor tab 68 on stacker table 90 comes close enough to travel limit sensor 72 so that travel limit sensor 72 can detect sensor tab 68. Once travel limit sensor 72 senses that stacker table 90 is in its uppermost position, stacker control turns off raising means 98. In this way, stacker control controls the position of stacker table 90.

Travel limit sensor 72 and home sensor 66 are commercially available visible light sensors. However, any other means for limiting the travel of stacker table 90 may also be used. For example, laser sensor, pneumatic, or hydraulic valves could be utilized. Alternatively, a nut placed on a lead screw could be used to stop to the travel of stacker table 90.

Also included in base 60 is a mechanism whereby microwell plates loaded in rack 40 may be easily removed from the bottom of the rack. As shown on FIG. 2A is rack door opening element 64. As also shown in FIG. 1B rack door opening element 64 opens rack door 44 to allow access to the microwell plates. Rack door opening element 64 can open rack door 44 when rack 40 is removably attached to base 60.

Referring again to FIG. 2A, housing 70 and surrounds the rest of the stacker base. Stacker control can be mounted on housing 70 or can be located externally.

Support 82 is attached to housing 70. As shown, supports 82 support grippers 84 on diametrically opposed sides of housing 70. Located on the inside surface of grippers 84 are rubber pads 86. Grippers 84 can be controlled by electronically stepper motors, by hydraulics, or by pneumatics. For instance if a pneumatic grippers are utilized, then by applying air pressure to grippers 84, grippers 84 move toward each other. By using commercially available valving techniques and applying air pressure in the other direction, the grippers 84 are forced away from each other. Regardless of whether stepper motors, hydraulics, or pneumatics are used, the location of the grippers 84, i.e., whether extended toward each other or withdrawn away from each other, is controlled by stacker control.

Also located on housing 70 is mounting bracket 88. Mounting bracket 88 connects plate orientation sensor 92. Each commercially available microwell plate generally has one of its four corners chamfered. These chamfered corners may be utilized to determine the orientation of a microwell plate. By knowing the location of the chamfered corner, it is possible to know the orientation of the microwell plate and thus positively identify each of the wells in the microwell plate. Without knowing the orientation of the microwell plate, it is possible that operations could be performed on the wrong well. By positively identifying the orientation of each microwell plate, the likelihood of occurrence of this problem is reduced.

Thus in this embodiment the plate orientation sensor 92 provides the required identification of the orientation of microwell plates. As a microwell plate is placed on the stacker table 90 and stacker table 90 is in its uppermost position, plate orientation sensor 92 detects to see whether the chamfered corner is presented or whether a non-chamfered corner, i.e., solid corner is present. Plate orientation sensor 92 can be a commercially available visible light sensor with two states. One state corresponds to the detection of a chamfered corner and one state corresponds to the detection of a non-chamfered corner of a microwell plate. Plate orientation sensor 92 sends a signal corresponding to its reading of the orientation of microwell plate to stacker control. If an non-chamfered signal is sent, stacker control ceases operation of the stacker and alerts an operator via an LED or other alarm mechanism. If a chamfered edge is detected, the microwell manipulation operation continues.

It can be noted that plate orientation 92 is located on housing 70. However, it is also possible that plate orientation sensor 92 could be of a laser variety and could be mounted to stacker base 96 Provided that the sensor can locate and determine the orientation of the microwell plates, any type of sensor could be utilized to allow the stacker 50 to operate properly.

Figure 2B:
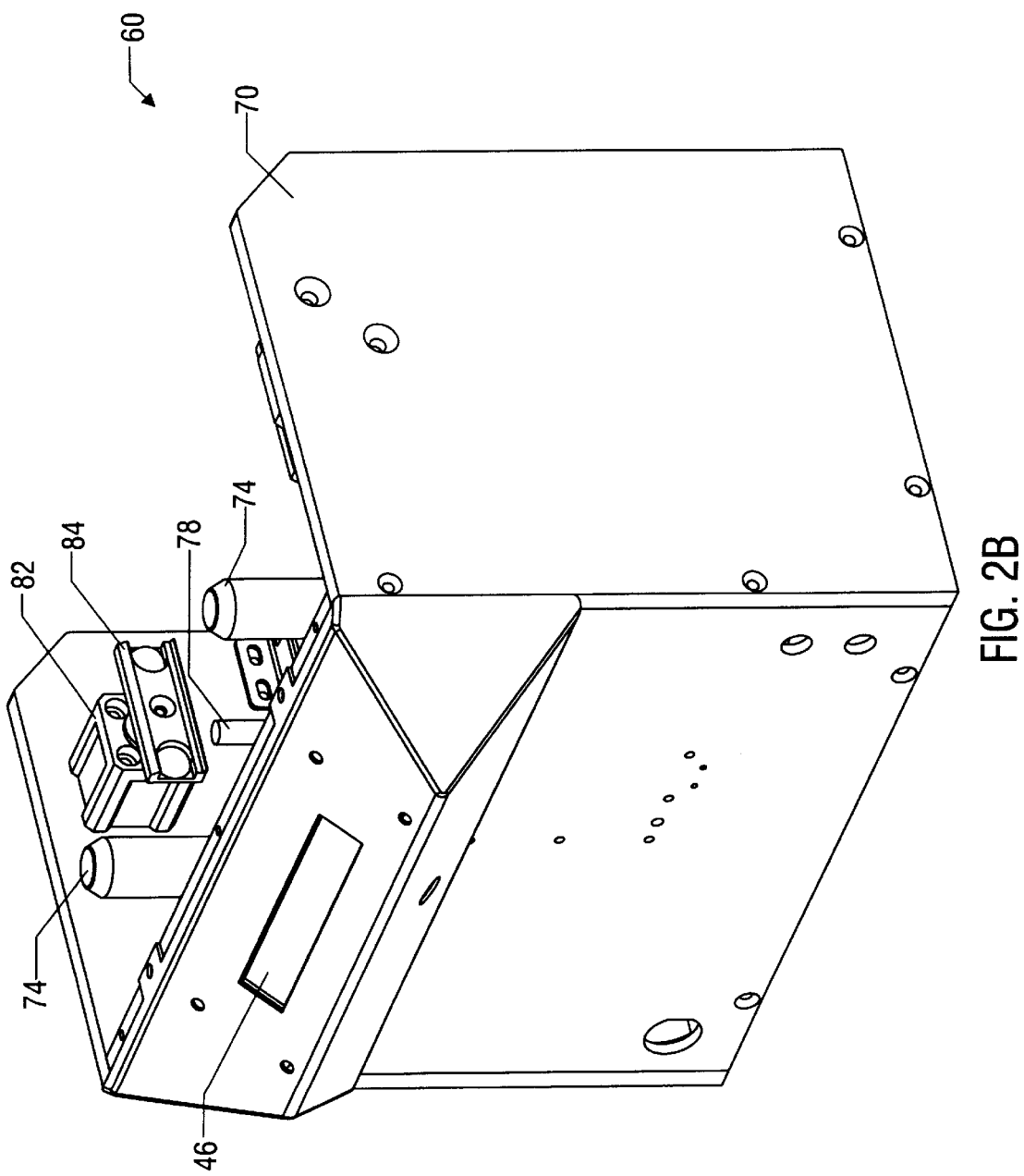
FIG. 2B illustrates the reverse angle view of the embodiment shown in FIG. 2A.

Referring to FIG. 2B, the back of the stacker base is shown. Stacker base 60 can contain user interface display 46. User interface display 46 can be used to inform an operator (not shown) of the status of the stacker. A signal from stacker control will be displayed on user interface display 46 to inform the operator of the status of the stacker. For example if the plate orientation sensor determines that a microwell plate is positioned in the wrong orientation, this information can be displayed on the user interface display.

Referring now to FIGS. 3A–3D, a simplified embodiment of stacker 50 is shown. FIG. 3A shows stacker table 90 in its lowest position and grippers 84 in their withdrawn position. Rack 40 is loaded with multiple microwell plates and with door 44 in its open position allowing free manipulation of the microwell plates. As shown in FIG. 3A, the weight of the microwell plates rests on stacker table 90. FIG. 3B shows the second step in the presentation cycle. Stacker control sends stacker table 90 to its uppermost position by powering raising means 98. FIG. 3B shows stacker table 90 in its uppermost position. As can be seen the multiple microwell plates also travel upwardly.

Referring to FIG. 3C, the third step in the presentation cycle is shown. Stacker table 90 is in its uppermost position. Stacker control extends grippers 84 to their extended position. Rubber pads 86 on grippers 84 contact the microwell plate in a position second to the lowest in the stack. The lowest microwell plate remains in contact with stacker table 90 and is undisturbed by the extension of grippers 84.

Referring to FIG. 3D, grippers 84 are in their extended position and stacker table 90 is in its lowermost position. As shown grippers 84 fully support the microwell plates remaining in the stacker. The lowest microwell plate remains in contact with stacker table 90. At this point, orientation sensor 92 detects the orientation of this lowest microwell plate. Provided the microwell is in the proper orientation, this microwell plate is now ready to be manipulated.

In this way the cycle is controlled by stacker control. Stacker control can be any commercially available control system such as a PC with software or a programmable logic controller, both of which are commercially available. Stacker control controls the location of the stacker table, the position of the grippers 84, the reading of the plate orientation sensor, and also sends appropriate messages to the user in a fixed display.

Because prior stackers do not have door 44, the picking up of the plate can only occur below the lowest portion of rack 40. This increases the height of the overall stacker mechanism which is disadvantageous if it is desired to enclose the work area. However, because this embodiment includes door 44, manipulation of the microwell plates is possible at a level above the lowest portion of rack 40. This compact design allows for significant savings of space in the work area.

Further, in prior stackers, if the bottom microwell plate were removed, the remaining microwell plates would suddenly drop down in the stacker: i.e. their fall would not be controlled. This can force fluid samples in each microwell plate to spill. However, because this embodiment includes grippers 84, the lowering of the remaining microwell plates is controlled.

Figure 4:
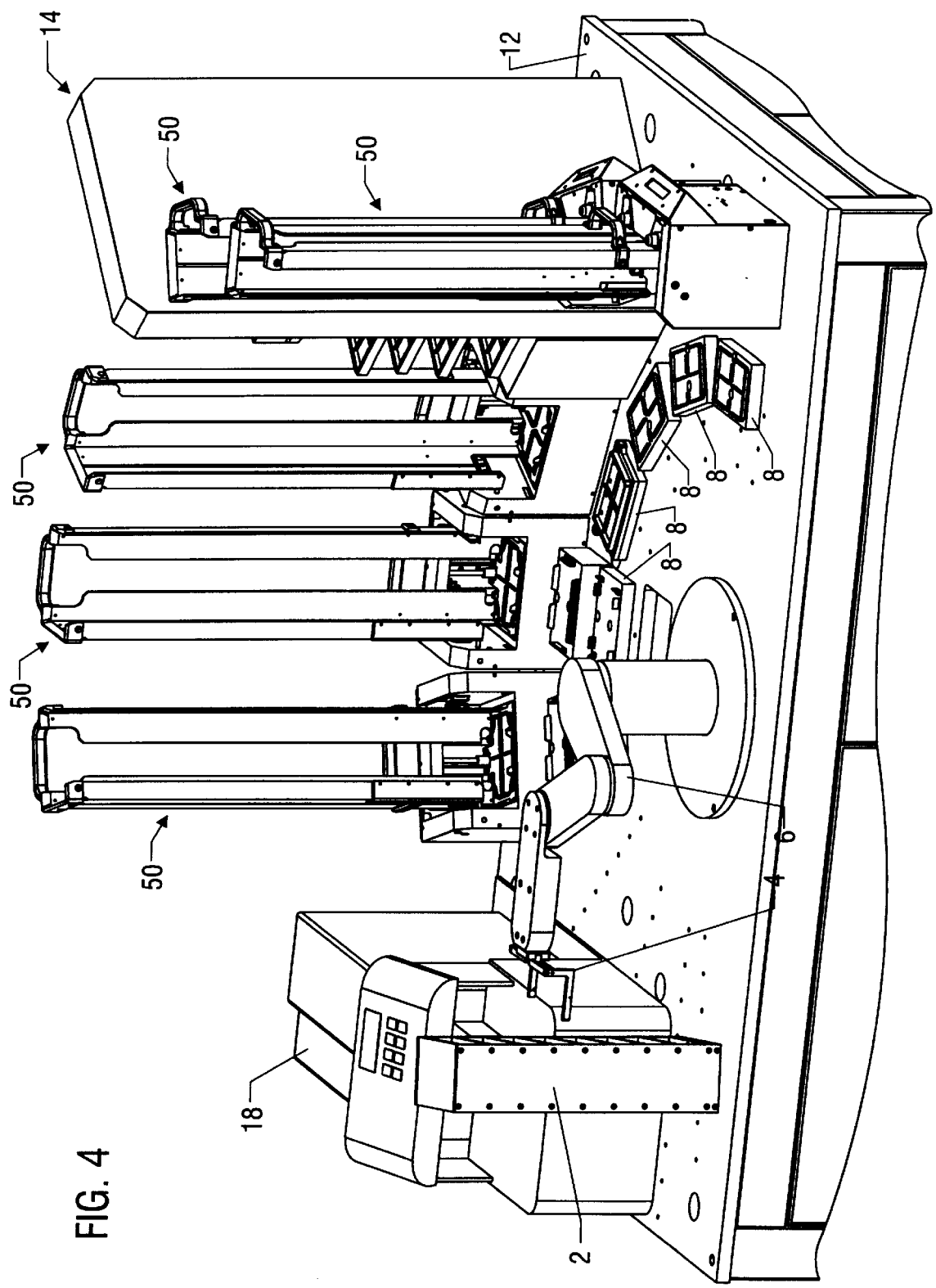
FIG. 4 shows an embodiment as used in a complete system for performing protocols.

Referring now to FIG. 4, a system is shown for performing various sample analysis protocols. Five stackers 50 are shown, although any number of stackers required for a particular protocol can be used. Further, in many instances, it is desirable to have this entire work area enclosed. After stacker 50 prepares a microwell plate for presentation, holder 4 on robot arm 6 will be directed to that stacker and lift that microwell plate from stacker table 90. At that point, the robot arm 6 can carry the microwell plate to a pipetting station 14 to dispense small amounts of liquid. Or the robot arm 6 can carry the microwell plate to hotel 2. Hotel 2 can be a heating station. For instance, in some sample analyses, it is required to combine reagents in a controlled environment at a particular temperature which is above ambient temperature. In these instances, hotel 4 acts as an oven in which this reaction may occur.

Hotel 4 could also possess light detectors. In this way, if clear microwell plates were utilized, light could shine one side of the microwell plate in the hotel. Detectors could reside on the hotel positioned on the other side of the microwell plate. These detectors could then determine, for example, the color of the sample in each cavity of the microwell plates.

Alternatively, robot arm 6 can carry the microwell plate to the various resting stations 8. Any number of procedures could be performed in this fashion. A barcoding station could be placed on table 12 to barcode the microwell plates. Or a plate washing cell could be placed on table 12. Any number of steps in a biological protocol could be performed. Once one particular Microwell plate has had all the steps performed as required by protocol, robot arm 60 can return the microwell plate to a stacker. Once all the microwell plates have gone through the protocol and are returned to a stacker, an operator (not shown) can remove the rack 40 from the stacker 50 and take the rack of completed microwell plates to another area for post-processing as required. By having the stackers 50 capable of independent manipulation and by utilizing resting stations 8 and hotel 2 along with any other station required by a given protocol, the micro biology protocols can be practiced in a flexible manner. This is a great advantage over prior art systems where conveyers are used and only one microwell plate can be processed in a given time. Other sample must wait until a microwell plate has completed or given protocol. Also because rack 40 is removable, the loading and unloading of microwell plates can be performed off-line or in another area thus freeing up the work area. Also because stacker 50 possesses door 44, access to the microwell plates is facilitated. Manipulation of the microwell plates can be performed in an area within rack 40 as compared to an area below rack 40 as required by prior art stackers. In these ways the stacker 50 provides for a more compact design for the manipulation of microwell plates.

The appended claims are intended to cover all such modifications and variations not limited to the specific embodiments which occur to one of ordinary skill in the art; the claims are not limited to the specific embodiments earlier described.

Although various embodiments have been shown and described, the invention is not so limited and will be understood to include all such modifications and variations as would be apparent to one skilled in the art.

What is claimed is:

1. A rack for storing, transporting, reloading, and dispensing sample carriers, comprising:
   at most three vertical corner sections, each vertical corner section having a top end and a bottom end; and
   a door functionally associated with said bottom end of one of said corner sections to allow access to said sample carrier.

2. The rack according to claim 1 further comprising two rack support brackets, each rack support bracket attached to the bottom end of a vertical corner section.

3. The rack according to claim 2 in which each rack support bracket is further provided with a cylindrical opening.

4. The rack according to claim 1 further comprising an orientation sensor functionally associated with said rack to detect the sample carrier orientation.

5. The rack according to claim 4 in which the orientation sensor is a visible light sensor.

6. The rack according to claim 4 in which the orientation sensor is a mechanical stop.

7. The rack according to claim 4 in which the orientation sensor is a laser.

8. A stacker apparatus for storing, transporting, reloading, and dispensing microwell plates, comprising:
   a rack having three vertical corner sections, each vertical corner section having a top end and a bottom end;
   a door functionally associated with said bottom end of one of said corner sections to allow access to said microwell plate;
   a base adapted to receive said rack, said base further comprising:
   a stacker table functionally associated with said base;
   a door opening element attached to said base, said element being positioned to contact said door on said rack;
   a plate gripper movably attached to said base;
   said rack detachably mounted to said base;
   each of said bottom ends of said corner sections of said rack being closer to said base than the top end of each of the corner sections; and
   a control functionally associated with said base.

9. The stacker according to claim 8 in which the plate gripper is provided with rubber pads.

10. The stacker according to claim 8 in which the control is a personal computer having controlling software.

11. The stacker according to claim 8 in which the control is a programmable logic controller.

12. The stacker according to claim 8 in which the base further comprises:
   raising means connecting the stacker table to the base, said raising means being controlled by the control;
   a linear bearing attached to said base and movably attached to said stacker table;
   a home sensor attached to the base;
   a travel limit sensor attached to the base, said stacker table having a sensor tab to trigger said home sensor and said travel limit sensor.

13. The stacker according to claim 8 in which the raising means is a stepper motor attached to the stacker table by a lead screw.

14. The stacker according to claim 8 in which the base further comprises a rack locating pin attached to said base for receiving the rack.

15. The stacker according to claim 14 in which the rack further comprises two rack support brackets, each rack support bracket attached to the bottom end of said vertical corner sections; said rack support brackets being mated with said rack locating pins positioned on said base.

16. The stacker according to claim 8 further comprising a plate orientation sensor attached to said base.

17. The stacker according to claim 16 in which the plate orientation sensor is a visible light sensor.

18. The stacker according to claim 16 in which the plate orientation sensor is a laser.

19. The stacker according to claim 16 in which the plate orientation sensor is a mechanical stop.

20. A stacker apparatus for storing, transporting, reloading, and dispensing microwell plates, comprising:
   means for storing microwell plates, said means having three vertical corner sections;
   means for supporting said means for storing microwell plates further comprising:
      a stacker table functionally associated with said means for supporting;
      means to grip microwell plates;
      means for removably attaching said means storing microwell plates to said means for supporting;
      raising means to elevate the stacker table;
   means for controlling the means for storing and means for supporting to load, unload, and store the microwell plates; and
   means for supporting the means for storing microwell plates at a prescribed height.

21. The stacker according to claim 20 in which the means for controlling is a personal computer having controlling software.

22. The stacker according to claim 20 in which the means to elevate is a stepper motor attached to the stacker table by a lead screw.

23. The stacker according to claim 20 further comprising a means for orienting said microwell plates, said means for orienting attached to said means for supporting.

24. The stacker according to claim 20 in which the means for controlling is a programmable logic controller.

25. The stacker according to claim 20 in which the means for gripping the microwell plates are provided with rubber pads.

26. The stacker according to claim 20 in which said means for storing microwell plates is provided with a door, said vertical corner sections having a top end and a bottom end, said bottom end of each vertical section closer to the supporting means than the top end, said door connected to the bottom end of one vertical section.

27. The stacker according to claim 26 in which the means for supporting is provided with a means for opening a door, said means for opening a door affixed to said means for supporting, said means for opening also being positioned to contact the door on the means for storing microwell plates.

28. A stacker apparatus for storing, transporting, and dispensing microwell plates, comprising:
   a rack having three vertical corner sections, each vertical corner section having a top end and a bottom end;
      a door functionally associated with said bottom end of one of said corner sections to allow access to said microwell plate; and
      two rack support brackets, each rack support bracket attached to the bottom end of said vertical corner sections;
   a base adapted to receive said rack, said base further comprising;
      a stacker table functionally associated with said base;
      a linear bearing attached to the base; said linear bearing movably attached to said stacker table;
      a door opening element attached to said base positioned to contact said door on said rack;
      a plate gripper movably attached to said base having rubber pads;
      raising means having a stepper motor, said raising means connected to the stacker table and the base;
      a home sensor attached to the base;
      a travel limit sensor attached to the base; said stacker table having a sensor tab to trigger said home sensor and said travel limit sensor;
      a plate orientation sensor attached to said base; said rack detachably mounted to said base;
      two rack supporting pins attached to the base for receiving said rack; and
   a personal computer functionally associated with said base to control the manipulation of the microwell plates;
      said rack support brackets being mated with said rack supporting pins located on said base;
      each of said bottom ends of said corner sections of said rack being closer to said base than the top end of each of the corner sections.

29. A method of storing, dispensing, reloading, and transporting microwell plates, comprising:
   providing a rack having three vertical corner sections;
   providing a base adapted to receive the rack; and
   controlling said rack and said base to manipulate said microwell plates.

30. A method of storing, dispensing, reloading, and transporting microwell plates, comprising:
   providing a stacker comprising:
      a rack having three vertical corner sections, each vertical corner section having a top end and a bottom end; a door functionally associated with said bottom end of one of said corner sections to allow access to said microwell plate;
      a base adapted to receive said rack, said base further comprising; a stacker table functionally associated with said base; a door opening element attached to said base positioned to contact said door on said rack;

a plate gripper movably attached to said base; said rack detachably mounted to said base; each of said bottom ends of said corner sections of said rack being closer to said base than the top end of each of the corner sections; and a control functionally associated with said base; and operating the control to manipulate the microwell plates.

31. The method of claim 30 further comprising determining the orientation of the microwell plates with an orientation sensor.

32. A stacker apparatus for four cornered sample carriers comprising:

a rack to contact at most three corners of the sample carriers when the sample carriers are inserted into the rack, the rack having a bottom;

a door functionally associated with the bottom of the rack to allow access to the sample carriers; and a base adapted to receive the bottom of the rack, said base having a door opening element that contacts the door to open the door on the rack when the rack is placed into the base, the rack being detachably mounted to said base.

33. The stacker apparatus of claim 32 further comprising a control functionally associated with said base.

34. The stacker apparatus of claim 33 further comprising a stacker table functionally associated with the base to manipulate the sample carriers.

35. The stacker apparatus of claim 34 further comprising a plate gripper movably attached to said base to selectively secure and release sample carriers.

36. The stacker apparatus of claim 35 further comprising an orientation sensor to sense the orientation of the sample carriers.

* * * * *